(12) United States Patent
Sebban Znaty et al.

(10) Patent No.: US 12,171,861 B2
(45) Date of Patent: Dec. 24, 2024

(54) LONG-LASTING COSMETIC COMPOSITION

(71) Applicants: CHANEL PARFUMS BEAUTE, Neuilly sur Seine (FR); ROQUETTE FRERES, Lestrem (FR)

(72) Inventors: Sarah Sebban Znaty, Pantin (FR); Aurélie Bonnefoy, Pantin (FR)

(73) Assignees: CHANEL PARFUMS BEAUTE, Neuilly sur Seine (FR); ROQUETTE FRERES, Lestrem (FR)

( * ) Notice: Subject to any disclaimer, the term of this patent is extended or adjusted under 35 U.S.C. 154(b) by 640 days.

(21) Appl. No.: 17/599,725

(22) PCT Filed: Mar. 27, 2020

(86) PCT No.: PCT/EP2020/058667
§ 371 (c)(1),
(2) Date: Sep. 29, 2021

(87) PCT Pub. No.: WO2020/201064
PCT Pub. Date: Oct. 8, 2020

(65) Prior Publication Data
US 2022/0192959 A1   Jun. 23, 2022

(30) Foreign Application Priority Data

Mar. 29, 2019 (FR) .................................... 19 03340

(51) Int. Cl.
| | | |
|---|---|---|
| *A61K 8/73* | (2006.01) | |
| *A61K 8/06* | (2006.01) | |
| *A61K 8/34* | (2006.01) | |
| *A61K 8/92* | (2006.01) | |
| *A61Q 1/10* | (2006.01) | |

(52) U.S. Cl.
CPC .............. *A61K 8/732* (2013.01); *A61K 8/062* (2013.01); *A61K 8/345* (2013.01); *A61K 8/922* (2013.01); *A61K 8/927* (2013.01); *A61Q 1/10* (2013.01)

(58) Field of Classification Search
CPC .................................. A61K 8/73; A61Q 1/10
IPC .......... A61K 8/732,8/062, 8/922, 8/927, 8/345; A61Q 1/10
See application file for complete search history.

(56) References Cited

U.S. PATENT DOCUMENTS

| | | |
|---|---|---|
| 5,871,756 A | 2/1999 | Jeffcoat et al. |
| 2002/0161104 A1 | 10/2002 | Labrousse et al. |
| 2007/0110799 A1 | 5/2007 | Leferve et al. |
| 2008/0112897 A1 | 5/2008 | Schiemann et al. |

FOREIGN PATENT DOCUMENTS

| | | | |
|---|---|---|---|
| JP | H10506921 A | 7/1998 | |
| JP | 2002241218 A | 8/2002 | |
| JP | 2003503316 A | 1/2003 | |
| JP | 2003095908 A | 4/2003 | |
| JP | 2007511584 A | 5/2007 | |
| JP | 2008543939 A | 12/2008 | |
| WO | WO-2010070234 A2 * | 6/2010 | ............... A61K 8/19 |
| WO | 2014/012918 A2 | 1/2014 | |
| WO | 2014097258 A2 | 6/2014 | |
| WO | 2014/155015 A1 | 10/2014 | |
| WO | 2018/114548 A1 | 6/2018 | |

OTHER PUBLICATIONS

International Search Report issued on Apr. 23, 2020 in corresponding International Application No. PCT/EP2020/058667; 6 pages.
Scott Hegenbart, "Understanding Starch Functionality", Natural Products Insider, Dec. 31, 1995, pp. 1-14; Retrieved from the Internet: https://www.naturalproductsinsider.com/print/16917 12 pages.

* cited by examiner

*Primary Examiner* — Walter E Webb
(74) *Attorney, Agent, or Firm* — Maier & Maier, PLLC

(57) ABSTRACT

A composition for coating keratin fibres, in the form of a wax-in-water emulsion including, in a first continuous aqueous phase, at least one legume starch having an amylose content greater than or equal to 30%, at least one plasticiser chosen among the polyols, at least one wax, at least one emulsifier and at least one colouring agent. Also, the use of such a composition in order to provide keratin fibres, in particular eyelashes, with a lengthening and curling effect.

20 Claims, No Drawings

LONG-LASTING COSMETIC COMPOSITION

The object of the present invention is a composition for coating keratin fibres, in the form of a wax-in-water emulsion comprising, in an aqueous continuous phase, at least one leguminous starch having an amylose content greater than or equal to 30%, at least one plasticiser selected from the polyols, at least one wax, at least one emulsifier, and at least one colouring agent. The invention also relates to the use of such a composition for conferring, on keratin fibres, in particular the eyelashes, an extending and curving effect.

FIELD

Products for making up or treating keratin materials are normally applied in the form of a uniform thin layer. For compositions intended for making up keratin fibres, for example mascaras, it is particularly desirable for the film deposited after the application to allow effective sheathing of the fibre, enabling it to be lengthened or curved. The mascara compositions currently available do not make it possible to form sufficiently sheathing films on the eyelashes. These films furthermore generally have a tendency to at least partly disintegrate, in particular by crumbling. Partial crumbling of the film results in a substantial loss of the intensity of the make-up colour.

BACKGROUND

To confer on mascaras properties of sheathing on the eyelashes, using film-forming polymers solubilised in a medium consisting of organic solvents is known.

Film-forming compositions at the present time use synthetic polymers such as polyvinylpyrrolidone (PVP) or polyvinyl acetate (PVA). However, consumers are more and more seeking cosmetic products composed mainly of natural ingredients or ingredients of natural origin, having the minimum number of chemical modifications. Eliminating synthetic functional ingredients, or replacing them with ingredients of natural origin, constitutes an important trend in developing novel cosmetic products. However, introducing these novel natural ingredients or ingredients of natural origin may be accompanied by a degradation of the properties of the cosmetic product, with regard to its appearance, its application or its cosmetic properties. These insufficient or degraded cosmetic properties are detrimental to the image of the product.

There therefore remains a need for a cosmetic composition using natural ingredients or ingredients of natural origin, capable of forming on the keratin fibres a continuous, homogeneous, extending, curving and long-lasting film that does not crumble, allowing easy make-up removal by peeling or with water.

SUMMARY

The applicant discovered unexpectedly that, by associating, in a wax-in-water emulsion, a highly-specific leguminous starch, a plasticiser and an emulsifier, it was possible to produce cosmetic compositions making it possible to form, on keratin fibres, a continuous, homogeneous and long-lasting deposit that does not crumble, to procure an extending and curving make-up for the eyelashes that is durable over time. Complete removal of the composition can be done by peeling or with water.

The object of the invention is thus, according to a first aspect, a wax-in-water cosmetic emulsion comprising:
- at least one leguminous starch having an amylose content greater than or equal to 30%, preferentially between 30% and 75%,
- at least one plasticiser selected from polyols,
- at least one wax,
- at least one emulsifier,
- at least one colouring agent, and
- water.

Another object of the invention, according to a second aspect, is a method for preparing such an emulsion, comprising:
- mixing water, plasticiser and optionally film-forming agent and optionally a preservative under stirring at a temperature greater than or equal to 90° C.,
- adding starch under stirring until a gel forms,
- optionally adding a gelling agent,
- optionally adding colouring agent,
- heating the wax to a temperature higher than or equal to 90° C. to enable said wax to melt,
- adding said molten wax and emulsifier to the mixture comprising water and the plasticiser under stirring to form the emulsion,
- cooling the emulsion obtained to ambient temperature under stirring,
- optionally adjusting the pH, and
- optionally adding alcohol.

Another object of the invention, according to a third aspect, is a method for making up keratinic materials, in particular keratin fibres such as the eyelashes or eyebrows, consisting of applying, to said keratin materials, in particular keratin fibres such as the eyelashes or eyebrows, an emulsion as described previously.

Finally, an object of the invention is the cosmetic use of an emulsion as described previously for conferring on keratin fibres, in particular the eyelashes, an extending and curving effect.

DETAILED DESCRIPTION

Galenic

The composition according to the invention is in the form of a wax-in-water emulsion.

Leguminous Starch

The emulsion according to the invention comprises at least one leguminous starch having an amylose content greater than or equal to 30%, preferentially between 30% and 75%.

In particular, the amylose content lies in a range from 30% to 75%, preferably from 30% to 45%, and preferably again from 35% to 40%. The percentages of amylose are expressed by dry weight, with respect to the dry weight of starch, and determined before any subsequent treatment such as hydrolysis and/or alkylation of said starch.

The leguminous starch also has a Brookfield viscosity in aqueous dispersion at 25° C. with 20% dry matter of between 10 and 10000 mPa·s, preferentially between 20 and 5000 mPa·s, more preferentially between 50 and 1000 mPa·s, most preferentially between 75 and 500 mPa·s, and even more preferentially around 150 mPa·s.

The viscosity within the meaning of the present invention is a Brookfield viscosity determined by means for example of a Brookfield RDVD-I+ viscometer (Brookfield Engineering Laboratories, INC. Middleboro, MA, USA) using one of the spindles referenced RV1, RV2, RV3, RV4, RV5, RV6 or RV7 and without the use of the equipment called "Helipath Stand". The rotation of the spindle is fixed at 20 revolutions per minute. The spindle, from RV1 to RV7, is selected so that the viscosity value displayed is between 10% and 100% of the total viscosity scale possible with said spindle, as indicated by the manufacturer. To make this measurement of viscosity, 300 ml of an aqueous suspension or aqueous solution with 20% by weight dry matter of starch prepared at 25° C. under mechanical stirring, for example with a deflocculating blade at 250 rpm for 15 minutes, is placed in a 400 ml low-shaped beaker (diameter approximately 7.5 cm). The viscosity value is taken at the end of the $3^{rd}$ rotation. The measurement is made in accordance with all the recommendations given by the manufacturer for obtaining a reliable viscosity measurement, for example in the manual "Operating Instructions, Manual No. M/92-021-M0101, Brookfield Digital Viscometer, Model DV-I+)".

The Brookfield viscosity in aqueous dispersion at 25° C. at 20% by weight dry matter is preferably between 10 and 10000 mPa·s, preferentially between 20 and 5000 mPa·s, more preferentially between 50 and 1000 mPa·s, most preferentially between 75 and 500 mPa·s, and even more preferentially around 150 mPa·s. These variants of Brookfield viscosity may be combined with the amylose content variants.

"Leguminous" within the meaning of the present invention means any plant belonging to the Caesalpiniaceae, Mimosaceae or Papilionaceae families and in particular any plant belonging to the Papilionaceae family such as for example peas, haricot beans, broad beans, horse beans, lentils or lupins.

Thus the leguminous starch can be selected from pea starches, chickpea starches, broad-bean starches, horse-bean starches, haricot-bean starches or lentil starches.

According to a preferred embodiment, the leguminous starch is a pea starch, and most preferentially a *Pisum sativum* starch.

Furthermore, the leguminous starch may be a pregelatinised native starch, or a chemically modified starch, optionally pregelatinised.

The chemically modified leguminous starches may be selected from the leguminous starches that have undergone at least one chemical modification, preferably at least two chemical modifications, selected from hydroxyalkylations, carboalkylations, hydrolyses, dextrinifications, succinylation, alkylation, acetylation, cationisation or anionisation. These chemical modifications are modifications for stabilising the leguminous starch, in other words stabilising the viscosity in aqueous solution, in that they make it possible to reduce or eliminate the retrogradation of a gel or of an aqueous solution of said starch.

Thus the modified leguminous starch used in the context of the present invention may be a hydroxyalkylated, carboxyalkylated or hydrolysed leguminous starch, a dextrin, or a combination thereof.

According to a preferred embodiment, the leguminous starch used in the context of the present invention is a hydrolysed and hydroxyalkylated leguminous starch. According to an especially preferred variant, the leguminous starch used in the context of the present invention is a hydrolysed and hydroxypropylated leguminous starch.

"Hydroxypropylated leguminous starch" within the meaning of the present invention means a leguminous starch substituted by hydroxypropyl groups by any technique known to a person skilled in the art, for example by etherification reaction with propylene oxide. In the context of the invention, a hydroxypropylated leguminous starch preferably has a hydroxypropyl group content of between 0.1 to 20% by dry weight, with respect to the dry weight of hydroxypropylated starch, preferentially between 1 and 10% by weight, more preferentially between 5 and 9% by weight, and in particular close to 7% by weight. This content is in particular determined by proton nuclear magnetic resonance spectrometry, in particular in accordance with EN ISO 11543:2002 F.

"Hydrolysed leguminous starch", within the meaning of the present invention, means a leguminous starch that has been subjected to a hydrolysis operation, i.e. an operation aimed at reducing the mean molecular mass thereof. A person skilled in the art knows how to obtain such starches, for example by chemical treatments such as oxidation and acid treatments, or by enzymatic treatments. A person skilled in the art will naturally adjust the level of hydrolysis, and therefore of fluidification, of the starch, according to the required viscosity.

In the context of the invention, a hydrolysed and optionally pregelatinized starch, and/or having chemical modifications other than described previously, preferably has a weight average molecular weight of between 1 and 2000 kDa, preferably 10 to 1000 kDa, most preferably 20 to 1000 kDa, and even more preferentially 100 to 1000 kDa. For example, the molecular weight may be from 200 to 800 kDa, from 200 to 500 kDa, from 200 to 400 kDa, or from 200 to 300 kDa. The weight average molecular weight being determined by HPSEC-MALLS (high-performance size-exclusion chromatography coupled with on-line multi-angle laser light scattering).

In particular, the starch after alkylation and hydrolysis will preferably be non-granular.

A hydrolysed and hydroxypropylated starch that can be used in a preferred manner in the context of the present invention is for example commercially available under the trade reference LYCOAT RS 720 or LYCOAT NG 720 from the company Roquette Frères.

Apart from these chemical modifications, the starch according to the invention may furthermore have undergone physical treatments, in particular selected from the known operations of gelatinisation, pre-gelatinisation, extrusion, atomisation or drying, microwave or ultrasound treatment operations, plasticisation or granulation.

In particular, the starch according to the invention may preferably be made soluble. It may be made soluble by any technique known to a person skilled in the art, in particular by heat and/or mechanical treatment, for example by a baking operation in an aqueous medium (pre-gelatinisation), optionally followed by a drying step when obtaining a powdery product is required. The operation aimed at making the starch soluble may entirely occur before or after the alkylation and/or the hydrolysis of the starch. According to a preferred embodiment, the hydrolysed and hydroxyalkylated starch is pre-gelatinised. Such a starch is commercially available under the trade reference LYCOAT RS 720 from the company Roquette Frères. Alternatively to pre-gelatinisation, it is possible to gelatinise the starch during the preparation of the composition in which it will be used.

The hydrolysed and hydroxyalkylated leguminous starch, optionally pre-gelatinised according to the invention, may also comprise any other physical and/or chemical modification, provided that this does not interfere with the required properties of said starch. One example of chemical modification is in particular crosslinking.

In particular in the context of the invention, the starch is present in a proportion of dry matter of between 0.1% and 25% by weight, preferably between 1% and 20% by weight, with respect to the total weight of the emulsion.

Plasticiser

The emulsion according to the invention also comprises at least one plasticiser selected from the polyols.

Polyol means any organic molecule having in the structure thereof at least two free hydroxy (—OH) groups. These polyols are preferably liquid at ambient temperature (25° C.).

By way of example of polyols suitable for use in the emulsion can be selected from propylene glycol, butylene glycol, pentylene glycol, pentanediol, isoprene glycol, neopentyl glycol, glycerol, polyethylene glycols (PEGs) having in particular from 4 to 8 ethylene glycol units, and/or sorbitol.

The polyols are preferably glycerol and sorbitol, preferably again in a mixture with pentylene glycol.

In a particularly preferred embodiment, the emulsion according to the invention does not comprise any plasticiser other than the polyols described above.

According to a particular embodiment, the emulsion according to the invention comprises from 8 to 25% by weight polyols, preferably from 10 to 20% by weight, with respect to the total weight of the emulsion.

In particular, the emulsion according to the invention may comprise:
  5 to 15% by weight glycerine with respect to the total weight of the composition,
  3 to 6% by weight sorbitol with respect to the total weight of the composition, and
  2 to 3% by weight pentylene glycol with respect to the total weight of the composition.

Aqueous Phase

The emulsion according to the invention also comprises an aqueous phase comprising water and optionally at least one water-soluble solvent other than the polyols described above.

"Water-soluble solvent" means, in the present invention, a compound liquid at ambient temperature and miscible with water (miscibility in water greater than 50% by weight at 25° C. and atmospheric pressure).

The water-soluble solvents that can be used in the compositions according to the invention may be volatile.

Among the water-soluble solvents that can be used in the compositions according to the invention, mention can be made in particular of the mono-alcohols having from 1 to 5 carbon atoms, in particular from 2 to 5 carbon atoms, such as ethanol and isopropanol, $C_3$-$C_3$ ketones and $C_2$-$C_4$ aldehydes.

According to a preferred embodiment, the composition according to the invention comprising at least one mono-alcohol having from 1 to 5 carbon atoms, in particular 2 to 5 carbon atoms, preferably ethanol.

Introducing a mono-alcohol having 1 to 5 carbon atoms, in particular 2 to 5 carbon atoms, facilitates and accelerates the drying of the film.

According to a particular embodiment, the emulsion according to the invention comprises from 25 to 60% by weight water, preferably from 30 to 50% by weight, with respect to the total weight of the emulsion.

Hydrophilic Gelling Agent

The emulsion according to the invention may also comprise a hydrophilic gelling agent.

Gelling agent, means a compound which, in the presence of a solvent, creates more or less strong intermacromolecular bonds thus giving rise to a three-dimensional lattice that fixes said solvent.

The hydrophilic gelling agent can be selected from polysaccharides, protein derivatives, synthesis or semisynthesis gels of the polyester type, in particular sulfonic, polyacrylates or polymethacrylates and the derivatives thereof.

Among the polysaccharides, mention can be made of:
  extracts of alga such as agar-agar, carrageenans (iota, kappa, lambda), alginates, in particular of Na or Ca;
  exudates of microorganisms such as xanthan gum and derivates thereof such as the product sold under the trade name "Rheosan" by the company Rhodia Chimie, the gellan gum sold under the trade name "Kelcogel F" by the company Nutrasweet-Kelco or the iota carrageenan sold under the trade names "Seaspan PF 357" or "Viscarin SD 389" by the company FMC, or the *Sclerotium* gum or *Sclerotium rolfssii* gum produced by the bacterium *Sclerotium rolfssii*, available under the name Naturajel® from the company DIY Cosmetics or Amigel® from the company Alban Muller;
  extracts of fruits such as pectins;
  gelling agents of animal origin such as protein derivatives, in particular gelatine, beef or fish, or caseinates;
  polysaccharides having a side chain and 6 neutral sugars as described in the document FR-A-2759377,
  and mixtures thereof.

Among polyacrylates, mention can be made of: cross-linked 25 EO polymers of acrylic acid, methylacrylate and polyoxyethylenated behenyl methacrylate (INCI name: Acrylates/Beheneth-25 Methacrylate Copolymer), such as the one sold under the name Novethix L-10 Polymer by the company Lubrizol Advanced Materials, or Rheostyl™ 90 N from Arkema (INCI: Acrylates/Beheneth-25 Methacrylate copolymer)

The hydrophilic gelling agent is preferably selected from polysaccharides, and preferably again from xanthan gum, *Sclerotium* gum, and a mixture thereof, for example the mixture sold under the name Actigum VSX 20 by the company Cargill.

According to a preferred embodiment, the mixture of xanthan gum and *Sclerotium* gum has a ratio by weight (xanthan:*Sclerotium*) of between 1:2 and 2:1.

The hydrophilic gelling agent is preferably present in the emulsion according to the invention at a concentration that may range from 0.1 to 10%, preferably again from 0.2 to 5%, by weight, with respect to the total weight of the emulsion.

Emulsifier

The emulsion according to the invention also comprises an emulsifier.

These emulsifiers can be selected from non-ionic, anionic, cationic or amphoteric surfactants or polymeric surfactants.

According to one embodiment, the surfactants that can be used in the context of the invention are selected from non-ionic surfactants with an HLB of between 8 and 20 at 25° C. Mention can be made in particular of:
  the esters and ethers of oses such as the mixture of cetylstearyl glucoside and of cetylic and stearyl alcohols such as Montanov 68 from Seppic;
  oxyethylenated and/or oxypropylenated glycerol ethers (which may include from 1 to 150 oxyethylenated and/or oxypropylenated groups);
  the oxyethylenated and/or oxypropylenated ethers (which may include from 1 to 150 oxyethylenated and/or oxypropylenated groups) of fatty alcohols (in particular C8-C24 and preferably C12-C18) such as oxyethylenated ether of cetearylic alcohol with 30 oxyethylenated groups (CTFA name "Ceteareth-30"), oxyethylenated stearyl alcohol ether with 20 oxyethylenated groups (CTFA name "Steareth-20"), oxyethylenated ether of the mixture of C12-C15 fatty alcohols including 7 oxyethylenated groups (CTFA name "C12-15 Pareth-7") in particular sold under the name NEODOL 25-7® by Shell Chemicals;

fatty acid esters (in particular of C8-C24 acid, and preferably C16-C22) and of polyethylene glycol (which may comprise from 1 to 150 ethylene glycol units) such as PEG-50 stearate and PEG-40 monostearate in particular, sold under the name MYRJ 52P® by the company ICI Uniquema, or PEG-30 glyceryl stearate in particular sold under the name TAGAT S® by the company Evonik Goldschmidt;

fatty acid esters (in particular of C8-C24 and preferably C16-C22 acid) and oxyethylenated and/or oxypropylenated glycerol ethers (which may include from 1 to 150 oxyethylenated and/or oxypropylenated groups), such as PEG-200 glyceryl monostearate in particular sold under the name Simulsol 220 TM® by the company Seppic; polyethoxylated glyceryl stearate with 30 ethylene oxide groups such as the product Tagat S® sold by the company Evonik Goldschmidt, polyethoxylated glyceryl oleate with 30 ethylene oxide groups such as the product Tagat O® sold by the company Evonik Goldschmidt, polyethoxylated glyceryl cocoate with 30 ethylene oxide groups such as the product Varionic LI 13® sold by the company Sherex, polyethoxylated glyceryl isostearate with 30 ethylene oxide groups such as the product Tagat L® sold by the company Evonik Goldschmidt and polyethoxylated glyceryl laureate with 30 ethylene oxide groups such as the product TAGAT I® from the company Evonik Goldschmidt, fatty acid esters (in particular of C8-C24 acid, and preferably C16-C22), and oxyethylenated and/or oxypropylenated sorbitol ethers (which may include from 1 to 150 oxyethylenated and/or oxypropylenated groups), such as polysorbate 20 in particular sold under the name Tween 20® by the company Croda, polysorbate 60 in particular sold under the name Tween 60® by the company Croda, dimethicone copolyol, such as the one sold under the name Q2-5220® by the company Dow Corning, dimethicone copolyol benzoate (Finsolv SLB 101® and 201® from the company Fintex), propylene oxide and ethylene oxide copolymers, also called OE/OP polycondensates, lysophospholipids, in particular the lysophosphatidylcholine with the following chemical formula [CHEM1]:

[Chem. 1]

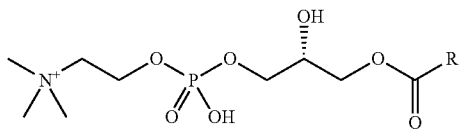

where R is a fatty acid chain, comprising in particular from 10 to 25 carbon atoms, preferably from 15 to 20. Preferably, the lysophospholipid used in the composition of the invention comes from soya seeds. Preferably again, its INCI name is glycine soya (soya bean) seed extract. For example, use is made of the mixture of glycerine at 80% by weight and of glycine soya (soya bean) seed extract at 20% by weight sold by Kemin by the name Lysofix Liquid®;

emulsifying waxes such as the autoemulsifying wax sold under the name Polawax NF by Croda, or the beeswax PEG=8 sold under the name Apifil by Gattefossé, and mixtures thereof.

According to a preferred embodiment, the emulsifier with an HLB of between 8 and 20 is selected from fatty acid esters and oxyethylenated and/or oxypropylenated sorbitol ethers, lysophospholipids, emulsifying waxes such as autoemulsifier waxes or hydrolysated waxes, and mixtures thereof.

Lysophospholipids such as Lysofix Liquid® afford a thickening of the composition, thus improving the spread thereof.

According to one embodiment, the surfactants that can be used in the emulsion according to the invention are selected from the non-ionic surfactants with an HLB of less than or equal to 8 at 25° C. Mention can be made in particular of:

the esters and ethers of oses such as sucrose stearate, sucrose cocoate, sorbitan stearate and mixtures thereof such as Arlatone 2121® sold by the company ICI;

the oxyethylenated and/or oxypropylenated ethers (which may include from 1 to 150 oxyethylenated and/or oxypropylenated groups) of fatty alcohols (in particular C8-C24, and preferably C12-C18, alcohol) such as oxyethylenated stearyl alcohol ether with 2 oxyethylenated groups (CTFA name "Steareth-2");

esters of fatty acids (in particular C8-C24 and preferably C16-C22 acid) and of polyol, in particular of glycerol or of sorbitol, such as glyceryl stearate, such as the product sold under the name TEGIN M® by the company Evonik Goldschmidt, glyceryl laureate such as the product sold under the name Imwitor 312® by the company Hüls, polyglyceryl-2 stearate, polyglyceryl-2 triisostearate, sorbitan tristearate and glyceryl ricinoleate;

lecithins, such as soya lecithins (such as Emulmetik 100 J from Cargill, or Biophilic H from Lucas Meyer);

the mixture of cyclomethicone/dimethicone copolyol sold under the name Q2-32250® by the company Dow Corning.

According to a preferred embodiment, the non-ionic surfactant with an HLB of less than or equal to 8 at 25° C. is selected from fatty acid and polyol esters, preferably polyglyceryl-2 triisostearate such as the one sold under the reference Cithrol PG32IS-LQ by the company Croda (INCI Polyglyceryl-3 Diisostearate).

The emulsion according to the invention may contain from 0.01 to 30% by weight emulsifier, with respect to the total weight of said emulsion, preferably from 0.1 to 15% by weight, and more preferentially from 0.2 to 13% by weight.

Film-Forming Agent

The emulsion according to the invention may also comprise an additional film-forming agent other than starch, in particular a film-forming polymer.

Among the film-forming polymers than can be used in the compositions of the present invention, mention can be made of synthetic polymers of the radical type or of the polycondensate type, polymers of natural origin, and mixtures thereof.

Radical film-forming polymer means a polymer obtained by polymerising unsaturated monomers, in particular ethylenic, each monomer being able to homopolymerise (unlike polycondensates).

The film-forming polymers of the radical type may in particular be vinyl polymers or copolymers, in particular acrylic polymers.

The vinyl film-forming polymers may result from the polymerisation of ethylenically unsaturated monomers having at least one acid group and/or esters of these acid monomers and/or amides of these acid monomers.

As a monomer carrying an acid group, use can be made of α,β ethylenically unsaturated carboxylic acids such as acrylic acid, methacrylic acid, crotonic acid, maleic acid or itaconic acid. Preferably use is made of methacrylic acid, itaconic acid and crotonic acid, and more preferentially itaconic acid (for example a metal salt of polyitaconic acid such as the one sold under the commercial reference RevCare NE 100S by the company Itaconix).

The esters of acid monomers are advantageously selected from esters of methacrylic acid (also referred to as methacrylates), in particular alkyl methacrylates, especially C1-C30 alkyl, preferably C1-C20, aryl methacrylates, in particular C6-C10 aryl, hydroxyalkyl methacrylates, in particular C2-C6 hydroxyalkyl.

Among alkyl methacrylates, mention can be made of methyl methacrylate, ethyl methacrylate, butyl methacrylate, isobutyl methacrylate, ethyl-2 hexyl methacrylate, lauryl methacrylate and cyclohexyl methacrylate.

Among the hydroxyalkyl methacrylates, mention can be made of hydroxyethyl acrylate, 2-hydroxypropyl acrylate, hydroxyethyl methacrylate and 2-hydroxypropyl methacrylate.

Among the aryl methacrylates, mention can be made of benzyl acrylate and phenyl acrylate.

The methacrylic acid esters that are particularly preferred are the alkyl methacrylates.

According to the present invention, the alkyl group of the esters may be either fluorinated or perfluorinated, that is to say some or all of the hydrogen atoms of the alkyl group are substituted by fluorine atoms.

As amides of the acid monomers, mention can be made for example of methacrylamides, and particular N-alkyl methacrylamides, especially C2-C12 alkyl. Among the N-alkyl methacrylamides, mention can be made of N-ethyl acrylamide, N-tert-butyl acrylamide, N-tert-octyl acrylamide and N-undecylacrylamide.

Vinyl film-forming polymers may also result from the homopolymerisation or copolymerisation of monomers selected from vinyl esters and styrene monomers. In particular, these monomers may be polymerised with acid monomers and/or esters thereof and/or amides thereof, such as those mentioned previously.

As an example of vinyl esters, mention can be made of vinyl acetate, vinyl neodeconoate, vinyl pivalate, vinyl benzoate and vinyl tert-butyl benzoate.

As styrene monomers, mention can be made of styrene and alpha-methyl styrene.

Among film-forming polycondensates, mention can be made of polyurethanes, polyesters, polyester amides, polyamides, and epoxyester resins, polyureas.

The polyurethanes may be selected from anionic, cationic, non-ionic or amphoteric polyurethanes, acrylic polyurethanes, polyurethane-polyvinylpyrrolidones, polyester-polyurethanes, polyether-polyurethanes, polyureas, polyureapolyurethanes, and mixtures thereof.

Polyesters can be obtained, in a known manner, by polycondensation of dicarboxylic acids with polyols, in particular diols.

The dicarboxylic acid may be aliphatic, alicyclic or aromatic. Mention can be made as an example of such acids: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornane dicarboxylic acid, diglycolic acid, thiodipropionic acid, 2,5-naphthalenedicarboxylic acid and 2,6-naphthalenedicarboxylic acid. These dicarboxylic acid monomers may be used alone or in combination of at least two dicarboxylic acid monomers. Among these monomers, preferably phthalic acid, isophthalic acid or terephthalic acid is selected.

The diol may be selected from aliphatic, alicyclic or aromatic diols. Use is preferably made of a diol selected from: ethylene glycol, diethylene glycol, triethylene glycol, 1,3-propanediol, cyclohexane dimethanol and 4-butanediol. As other polyols, use can be made of glycerol, pentaerythritol, sorbitol or trimethylol propane.

Polyester amides can be obtained in a similar manner to polyesters, by polycondensation of diacids with diamines or amine alcohols. As a diamine, use can be made of ethylenediamine, hexamethylenediamine, meta- or para-phenylenediamine. As amino alcohol, monoethanolamine can be used.

The polyester may furthermore comprise at least one monomer carrying at least one —SO3M group, with M representing a hydrogen atom, an ammonium ion NH4+ or a metal ion, such as for example an Na+, Li+, K+, Mg2+, Ca2+, Cu2+, Fe2+, Fe3+ ion. In particular a bifunctional aromatic monomer including such a —SO3M group can be used.

The aromatic core of the bifunctional aromatic monomer furthermore carrying a —SO3M group as described above can be selected for example from benzene, naphthalene, anthracene, diphenyl, oxydiphenyl, sulfonyldiphenyl or methylenediphenyl cores. Mention can be made, as an example of a bifunctional aromatic monomer furthermore carrying a —SO3M group, of: sulfoisophthalic acid, sulfoterephthalic acid, sulfophthalic acid, 4-sulfonaphthalene-2, 7-dicarboxylic acid.

It is preferred to use copolymers based on isophthalate/sulfoisophthalate, and more particularly copolymers obtained by condensation of di-ethyleneglycol, cyclohexane di-methanol, isophthalic acid or sulfoisophthalic acid.

The polymers of natural origin, optionally modified, can be selected from shellac resin, sandarac gum, gum arabic (acacia senegal gum), dammars, elemis, copals, cellulose polymers, polymers extracted from the fruit of *Caesalpinia spinosa* and/or from the alga *Kappaphycus alvarezii* (such as the product Filmexel® sold by the company Silab), and mixtures thereof. A natural polymer such as Filmexel® in particular improves the strength of the film obtained from the composition according to the invention.

According to a first embodiment of the invention, the film-forming polymer may be a water-soluble polymer and may then be present in the aqueous continuous phase of the composition according to the invention.

According to a second embodiment, the film-forming polymer may also be present in a composition of the invention in the form of particles in dispersion. In an aqueous phase or in a non-aqueous solvent phase, generally known by the term latex or pseudolatex. The techniques for preparing these dispersions are well known to persons skilled in the art.

As an aqueous dispersion of film-forming polymer, use can be made of the acrylic dispersion sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasei Kogyo; Syntran 5760® by the company Interpolymer, Allianz OPT by the company Rohm & Haas, the aqueous dispersions of acrylic or styrene-acrylic polymers sold under the brand name Joncryl® by the company Johnson Polymer or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer, Aquamere H-1511® by the company Hydromer; the sulfopolyesters sold under the brand name Eastman AQ® by the company Eastman Chemical Products, vinyl dispersions such as Mexomere PAM® by the company Chimex and mixtures thereof.

As examples of non-aqueous dispersions of film-forming polymer, mention can be made of acrylic dispersions in isododecane such as Mexomere PAP® from the company CHIMEX, dispersions of particles of a grafted ethylene polymer, preferably acrylic, in a liquid fatty phase, the ethylene polymer advantageously being dispersed in the absence of an additional stabiliser on the surface of the particles as described in particular in the document WO 04/055081.

According to a third embodiment, the film-forming polymer may be a polymer solubilised in a liquid fatty phase comprising oils or organic solvents (it is then said that the film-forming polymer is a liposoluble polymer).

By way of example of liposoluble polymer, mention can be made of the vinyl ester copolymers (the vinyl group being directly bonded to the oxygen atom of the ester group and the vinyl ester having a saturated hydrocarbon radical, linear or branched, from 1 to 19 carbon atoms, bonded to the carbonyl of the ester group) and of at least one other monomer that may be a vinyl ester (different from the vinyl ester already present), an α-olefin (having from 8 to 28 carbon atoms), an alkyl vinyl ether (the alkyl group of which includes 2 to 18 carbon atoms), or an allyl or methallyl ester (having a saturated hydrocarbon radical, linear or branched, from 1 to 19 carbon atoms, bonded to the carbonyl of the ester group).

These copolymers may be crosslinked by means of crosslinking agents that may be either of the vinyl type or of the allyl or methallyl type, such as tetraallyloxyethane, divinylbenzene, divinyl octanedioate, divinyl dodecanedioate and divinyl octadecanedioate.

As examples of these copolymers, mention can be made of the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/octadecene-1, vinyl acetate/dodecene-1, vinyl stearate/ethyl vinyl ether, vinyl propionate/cetyl vinyl ether, vinyl stearate/allyl acetate, vinyl dimethyl-2,2-octanoate/vinyl laurate, allyl dimethyl-2,2-pentanoate/vinyl laurate, vinyl dimethyl propionate/vinyl stearate, allyl dimethyl propionate/vinyl stearate, vinyl propionate/vinyl stearate, crosslinked with 0.2% divinyl benzene, vinyl dimethyl propionate/vinyl laurate, crosslinked with 0.2% divinyl benzene, vinyl acetate/octadecyl vinyl ether, crosslinked with 0.2% tetraallyloxyethane, vinyl acetate/allyl stearate, crosslinked with 0.2% divinyl benzene, vinyl acetate/octadecene-1 crosslinked with 0.2% divinyl benzene, and allyl propionate/allyl stearate crosslinked with 0.2% divinyl benzene.

As liposoluble film-forming polymers, mention can also be made of liposoluble copolymers, and in particular those resulting from copolymerisation of vinyl esters having from 9 to 22 carbon atoms or alkyl acrylates or methacrylates, or allyl radicals having from 10 to 20 carbon atoms.

Such liposoluble copolymers may be selected from the copolymers of vinyl polystearate, of vinyl polystearate crosslinked by means of divinyl benzene, of diallyl ether or of diallyl phthalate, the copolymers of stearyl polymethacrylate, of vinyl polylaurate, of lauryl polymethacrylate, these polymethacrylates being able to be crosslinked by means of methylene glycol dimethacrylate or tetraethylene glycol.

The liposoluble copolymers defined above are known and in particular described in the application FR-A-2232303; they may have a weight average molecular weight ranging from 2000 to 500,000 and preferably from 4000 to 200,000.

Mention can also be made of the liposoluble homopolymers, and in particular those resulting from the homopolymerisation of vinyl esters having from 9 to 22 carbon atoms or of alkyl acrylates or methacrylates, the alkyl radicals having from 2 to 24 carbon atoms.

As examples of liposoluble homopolymers, mention can be made in particular of: vinyl polylaurate and lauryl polymethacrylates, these polymethacrylates being able to be crosslinked by means of ethylene glycol dimethacrylate or tetraethylene glycol.

As liposoluble film-forming polymers that can be used in the invention, mention can also be made of polyalkylenes and in particular the copolymers of C2-C20 alkenes, such as polybutene, alkylcelluloses with a C1 to C8 linear or branched alkyl radical, saturated or not, such as ethylcellulose and propylcellulose, copolymers of vinylpyrrolidone (VP) and in particular the copolymers of vinylpyrrolidone and C2 to C40 and better C3 to C20 alkene. By way of example of a copolymer of VP that can be used in the invention, mention can be made of the copolymer of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene, and VP/methacrylic acid/lauryl methacrylate.

Mention can also be made of silicone resins, generally soluble or swellable in silicone oils, which are crosslinked polyorganosiloxane polymers. Silicone resins are known by the name "MDTQ", the resin being described according to the various siloxane monomeric units that it comprises, each of the letters "MDTQ" characterising a type of the unit.

By way of examples of commercially available polymethylsilsesquioxane resins, mention can be made of those that are sold by the company Wacker under the reference Resin MK, such as Belsil PMS MK, and by the company Shin-Etsu under the references KR-220L.

As siloxysilicate resins, mention can be made of the trimethylsiloxysilicate (TMS) resins such as those sold under the reference SR1000 by the company General Electric or under the reference TMS 803 by the company Wacker. Mention can also be made of the trimethylsiloxysilicate resins sold in a solvent such as cyclomethicone, sold under the name "KF-7312J" by the company Shin-Etsu, and "Dowsil™ RSN-0749" and "Dowsil™ 593 Fluid" by the company Dow Corning.

Mention can also be made of the copolymers of silicone resins such as those cited above with polydimethylsiloxanes, such as the pressure-sensitive adhesive copolymers sold by the company Dow Corning under the reference BIO-PSA and those described in the document U.S. Pat. No. 5,162,410 or the silicone copolymers resulting from the reaction of a silicone resin, such as those described above, and of a diorganosiloxane such as those described in the document WO 2004/073626.

Finally, mention can be made of acrylate/polytrimethylsiloxymethacrylate copolymer comprising a dendrimer carboxysiloxane structure grafted onto a vinyl skeleton available commercially under the references Dow Corning FA 4002 ID or Dow Corning FA 4001 CM.

Use can also be made of the silicone polyamides of the polyorganosiloxane type such as those described in the documents U.S. Pat. Nos. 5,874,069, 5,919,441, 6,051,216 and 5,981,680.

According to a preferred embodiment, the additional film-forming polymer is selected from the polymers of natural origin, optionally modified, preferably from the polymers extracted from the fruit of *Caesalpinia spinosa* and/or from the alga *Kappaphycus alvarezii* (such as the product Filmexel® sold by the company Silab).

In a preferred embodiment, the composition according to the invention does not comprise any film-forming polymer other than the leguminous starch.

Silicone Elastomers

The emulsion according to the invention may also comprise a silicone elastomer.

Adding a silicone elastomer makes it possible in particular to limit the phenomenon of fluffing liable to manifest when the composition according to the invention is applied.

Among these, mention can be made of the at least partially crosslinked polymers resulting from the reaction of an organopolysiloxane carrying unsaturated groups, such as vinyl or allyl groups, located at the end or at the middle of a chain, preferably on a silicon atom, with another reactive silicone compound such as an organohydrogenopolysiloxane. These polymers are normally available in the form of a gel in a volatile or non-volatile silicone solvent or in a hydrocarbon solvent. Examples of such elastomers are in particular sold by the company Shin-Etsu under the trade names KSG-6, KSG-16, KSG-31, KSG-32, KSG-41, KSG-42, KSG-43 and KSG-44, and by the company Dow Corning under the trade names Dowsil™ 9040 and Dowsil™ 9041. Another oily gelling agent consists of a silicone polymer, obtained by auto-polymerisation of an organopolysiloxane functionalised by epoxy groups and hydrosilylated in the presence of a catalyst, which is commercially available from the company General Electric under the trade name Velvesil® 125. Another lipophilic gelling agent consists of a cyclic dimethicone/vinyldimethicone copolymer such as the one sold by the company Jeen under the trade name Jeesilc® PS (including PS-VH, PS-VHLV, PS-CM, PS-CMLV and PS-DM).

According to a preferred embodiment, the silicone elastomer may be emulsifying, preferably selected from the polyoxyalkylenated and polyglycerolated silicone elastomers.

As polyoxyalkylenated silicone elastomers, mention can be made of those described in the U.S. Pat. Nos. 5,236,986, 5,412,004, 5,837,793, 5,811,487.

As polyoxyalkylenated silicone elastomers, the following can be used: those with the INCI name PEG-10 Dimethicone/Vinyl dimethicone crosspolymer: such as those sold under the names "KSG-21", "KSG-20", by Shin-Etsu; those with the INCI name Lauryl PEG-15 Dimethicone/Vinyldimethicone Crosspolymer: such as those sold under the names "KSG-30" and "KSG-31", KSG-32" (in isododecane), "KSG-33" (in trioctanoin), "KSG-210", "KSG-310" (in a mineral oil), "KSG-320" (in isododecane), "KSG-330", "KSG-340" by the company Shin-Etsu.

As polyglycerol silicone elastomers, the following can be used: —those with the INCI name Dimethicone (and) Dimethicone/Polyglycerin-3 crosspolymer: such as those sold under the names "KSG-710" by Shin-Etsu; those with the INCI name Lauryl Dimethicone/Polyglycerin-3 crosspolymer: such as those sold under the names "KSG-840" (in squalene) by the company Shin-Etsu.

Oils

The emulsion according to the invention may comprise at least one oil selected from volatile oils and/or non-volatile oils, and mixtures thereof.

"Volatile oil" means, within the meaning of the invention, an oil liable to evaporate in contact with keratin fibres in less than one hour, at ambient temperature and atmospheric pressure. The volatile organic solvent or solvents and the volatile oils of the invention are organic solvents and volatile cosmetic oils, liquid at ambient temperature, having a non-zero vapour pressure, at ambient temperature and atmospheric pressure, ranging in particular from 0.13 Pa to 40,000 Pa ($10^{-3}$ at 300 mm of Hg), in particular ranging from 1.3 Pa to 13,000 Pa (0.01 to 100 mm of Hg), and more particularly ranging from 1.3 Pa to 1300 Pa (0.01 to 10 mm of Hg).

The volatile oil may be hydrocarbon. The hydrocarbon volatile oil may be selected from the hydrocarbon oils having from 7 to 16 carbon atoms. As a hydrocarbon volatile oil having from 7 to 16 carbon atoms, mention can be made in particular of the C8-C16 branched alkanes such as the C8-C16 iso-alkanes (also called isoparaffins), isododecane, isodecane, isohexadecane and for example the oils sold under the trade names Isopars or Permetyls, the C8-C16 branched esters such as iso-hexyl neopentanoate, and mixtures thereof. Preferably the hydrocarbon volatile oil having from 8 to 16 carbon atoms is selected from isododecane, isodecane, isohexadecane and mixtures thereof, and is in particular isododecane.

The volatile oil may be a volatile linear alkane. According to one embodiment, an alkane suitable for the invention may be a volatile linear alkane comprising from 7 to 14 carbon atoms. Such a volatile linear alkane may advantageously be of plant origin. By way of example of alkanes suitable for the invention, mention can be made of the alkanes described in the patent applications of the company Cognis WO 2007/1068371, or WO 2008/155059 (distinct mixtures of alkanes differing by at least one carbon atom). These alkanes are obtained from fatty alcohols, themselves obtained from copra or palm oil. By way of example of linear alkanes suitable for the invention, mention can be made of n-heptane (C7), n-octane (C8), n-nonane (C9), n-decane (C10), n-undecane (C11), n-dodecane (C12), n-tridecane (C13), n-tetradecane (C14), and mixtures thereof. According to a particular embodiment, the volatile linear alkane is selected from n-nonane, n-undecane, n-dodecane, n-tridecane, n-tetradecane, and mixtures thereof. According to a preferred embodiment, mention can be made of the mixtures of n-undecane (C11) and n-tridecane (C13) obtained at examples 1 and 2 of the application WO 2008/15505 of the company Cognis. Mention can also be made of the mixture of n-undecane (C11) and n-tridecane (C13) sold by the company BASF under the name Cetiol Ultimate. Mention can also be made of the n-dodecane (C12) and the n-tetradecane (C14) sold by Sasol respectively under the references PARAFOL 12-97 and PARAFOL 14-97, as well as mixtures thereof. It will be possible to use the volatile linear alkane alone or preferentially a mixture of at least two distinct volatile linear alkanes, differing from each other by a number of carbon atoms of at least 1, in particular differing from each other by a number of carbon atoms of 1 or 2.

The volatile oil may be a volatile silicone oil such as cyclic polysiloxanes linear polysiloxanes and mixtures thereof. As linear volatile polysiloxanes, mention can be made of hexamethyldisiloxane, octamethyltrisiloxane, decamethyltetrasiloxane, tetradecamethylhexasiloxane and hexadecamethylheptasiloxane. As cyclic volatile polysiloxanes, mention can be made of hexamethylcyclotrisiloxane, octamethylcylotetrasiloxane, decamethylcyclopentasiloxane and dodecamethylcyclohexasiloxane.

In a variant or additionally, the composition produced may comprise at least one fluorinated volatile oil.

"Non-volatile oil" means an oil remaining on the keratin fibres at ambient temperature and atmospheric pressure at least for several hours and having in particular a vapour pressure of less than $10^{-3}$mm of Hg (0.13 Pa).

The non-volatile oils may in particular be selected from hydrocarbon or fluorinated oils and/or non-volatile silicone oils.

As non-volatile hydrocarbon oil, mention can be made in particular of:

hydrocarbon oils of animal origin, hydrocarbon oils of plant origin such as the C4 to C36 linear alkanes, preferably C11-C21, such as phytosqualane or Emogreen L15 from Seppic (C15-C19 alkane), or such as the phytostearyl esters such as phytostearyl oleate, phytostearyl isostearate and lauroyl/octyldodecyl/phytostearyl glutamate (Ajinomoto, Eldew PS203), triglycerides consisting of fatty acid esters and of glycerol, in particular wherein the fatty acids may have chain lengths varying from C4 to C36, and in particular from C18 to C36; these oils being able to be linear or branched, saturated or unsaturated; these oils may in particular be heptanoic or octanoic triglycerides, shea, alfalfa, poppy seed, Chinese okra, millet, barley, quinoa, rye, candleberry or passionflower oil, shea butter, aloe oil, sweet almond oil, peach kernel oil, groundnut oil, argan oil, avocado oil, baobab oil, borage oil, broccoli oil, calendula oil, camelina oil, carrot oil, safflower oil, hemp oil, colza oil, cotton oil, copra oil, marrow seed oil, wheatgerm oil, jojoba oil, lily oil, macadamia oil, maize oil, meadowfoam oil, St. John's wort oil, scented coconut oil, hazelnut oil, apricot kernel oil, walnut oil, olive oil, evening primrose oil, palm oil, blackcurrant pip oil, kiwi pip oil, grapeseed oil, pistachio oil, Chinese okra oil, pumpkin oil, quinoa oil, muscat rose oil, sesame oil, soya oil, sunflower seed oil, castor oil and watermelon oil, and mixtures thereof, or caprylic/capric acid triglycerides, such as those sold by the company Stearineries Dub0is or those sold under the names Miglyol 810®, 812® and 818® by the company Dynamit Nobel, synthesis ethers having from 10 to 40 carbon atoms;

synthesis esters such as the oils of formula R1 COOR2, wherein R1 represents a residue of a linear or branched fatty acid including from 1 to 40 carbon atoms and R2 represents a hydrocarbon chain, in particular branched containing 1 to 40 carbon atoms provided that R1+R2 is ≥10. The esters may in particular be selected from alcohol and fatty acid esters, such as for example cetostearyl octanoate, isopropyl alcohol esters, such as isopropyl myristate, isopropyl palmitate, ethyl palmitate, 2-ethylhexyl palmitate, isopropyl stearate or isostearate, isostearyl isostearate, octyl stearate, hydroxylated esters, such as isostearyl lactate, octyl hydroxystearate, diisopropyl adipate, heptanoates, and in particular isostearyl heptanoate, octanoates, decanoates or ricinoleates of alcohols or polyalcohols, such as propylene glycol dioctanoate, cetyl octanoate, tridecyl octanoate, 4-diheptanoate and 2-ethylhexyl palmitate, alkyl benzoate, polyethylene glycol diheptanoate, propylene glycol 2-diethylhexanoate and mixtures thereof, C12-C15 alcohol benzoates, hexyl laurate, neopentanoic acid esters, such as isodecyl neopentanoate, isotridecyl neopentanoate, isostearyl neopentanoate, octyldocecyl pentanoate, isononanoic acid esters, such as isononyl isononanoate, isotridecyl isononanoate, octyl isononanoate, hydroxylated esters such as isostearyl lactate, di-isostearyl malate;

polyol esters and pentaerythritol esters, such as dipentaerythritol tetrahydroxystearate/tetraisostearate, dimer diol esters and dimer diacid esters, such as Lusplan DD-DA5® and Lusplan DD-DA7®, sold by the company Nippon Fine Chemical and described in the application US 2004-175338, dimer diol and dimer diacid copolymers and esters thereof, such as the dimer dilinoleyl diol/dimer dilinoleic copolymers and esters thereof, such as for example Plandool-G, polyol and dimer diacid copolymers, and esters thereof, such as Hailuscent ISDA, the fatty alcohols liquid at ambient temperature with a branched and/or unsaturated carbon chain having from 12 to 26 carbon atoms, such as 2-octyldodecanol, isostearyl alcohol, oleic alcohol, 2-hexyldecanol, 2-blatyloctanol, and 2-undecylpentadecanol, $C_{12}$-$C_{22}$ higher fatty acids, such as oleic acid, linoleic acid and mixtures thereof, di-alkyl carbonates, the 2 alkyl chains being able to be identical or different, such as the dicaprylyl carbonate sold by the name Cetiol CC®, by Cognis, oils with a high molar mass having in particular a molar mass ranging from approximately 400 to approximately 10000 g/mol, in particular from approximately 650 to approximately 10000 g/mol, in particular from approximately 750 to approximately 7500 g/mol, and more particularly varying from approximately 1000 to approximately 5000 g/mol, silicone oils, such as phenylated silicones such as BELSIL PDM 1000 of the company Wacker (MM=9000 g/mol). Other non-volatile silicone oils that can be used in the composition according to the invention can be the non-volatile polydimethylsiloxanes (PDMSs), the PDMSs including pendant alkyl or alkoxy groups and/or silicone end of chain groups, groups each having from 2 to 24 carbon atoms, phenylated silicones, such as phenyl trimethicones, phenyl dimethicones, phenol trimethylsiloxy diphenylsiloxanes, diphenyl dimethicones, diphenyl methyldiphenyl trisiloxanes, and 2-phenylethyl trimethylsiloxysilicates, dimethicones or phenyltrimethicones with a viscosity of less than or equal to 100 cSt, and mixtures thereof, the fluorinated oils that can be used in the invention are in particular fluorosilicone oils, fluorinated polyethers and fluorinated silicones as described in the document EP-A-847752.

Waxes

The emulsion according to the invention comprises at least one wax.

The wax considered in the context of the present invention is in general terms a lipophilic compound, solid at ambient temperature (25° C.), with a reversible solid/liquid change of state, having a melting point higher than or equal to 30° C., which may range up to 120° C.

In particular, the waxes suitable for the invention may have a melting point above approximately 45° C., and in particular above 55° C. The melting point of the wax can be measured by means of a differential scanning calorimeter (D.S.C.), for example the calorimeter sold by the name DSC 30 by the company Metler.

The waxes able to be used in the compositions according to the invention are selected from solid waxes, deformable or not at ambient temperature, of animal, vegetable, mineral or synthetic origin and mixtures thereof.

The wax may also have a hardness ranging from 0.05 MPa to 30 MPa, and preferably ranging from 6 MPa to 15 MPa. The hardness is determined by measuring the compressive force measured at 20° C. using the texturometer sold by the name TA-TX2i by the company Rheo, equipped with a stainless steel cylinder with a diameter of 2 mm moving at the measuring speed of 0.1 mm/s, and penetrating the wax to a penetration depth of 0.3 mm.

It is in particular possible to use hydrocarbon-based waxes such as beeswax, lanolin wax, and Chinese insect waxes; rice wax, carnauba wax, candellila wax, ouricurry wax, asparto grass wax, cork-fibre wax, sugar cane wax, Japan wax and sumac wax; montan wax, microcrystalline waxes, paraffins and ozokerite; beeswax, jojoba wax, mimosa wax, sunflower wax, polyethylene waxes, waxes obtained by Fisher-Tropsch synthesis and waxy copolymers as well as esters thereof. A mixture of jojoba wax, mimosa wax and sunflower wax is for example sold under the reference ACTICIRE MP by the company Gattefossé. In particular, the hydrocarbon-based waxes may be selected from Carnauba wax, beeswax, jojoba wax, mimosa wax, sunflower wax and mixtures thereof.

Mention can also be made of the waxes obtained by catalytic hydrogenation of animal or vegetable oils having $C_8$-$C_{32}$ linear or branched fatty chains.

Among these, mention can in particular be made of hydrogenated jojoba oil, hydrogenated sunflower oil, hydrogenated ricin oil, hydrogenated copra oil and hydrogenated lanolin oil, di-(trimethylol-1,1,1 propane) tetrastearate sold under the name "HEST 2T-4S" by the company Heterene, di-(trimethylol-1,1,1 propane) tetrabehenate sold under the name HEST 2T-4B by the company Heterene.

Use can also be made of the waxes obtained by transesterification and hydrogenation of vegetable oils, such as ricin or olive oil, such as the waxes sold under the names Phytowax Ricin 16L64® and 22L73® and Phytowax Olive 18L57 by the company Sophim. Such waxes are described in the application FR-A-2792190.

Use can also be made of silicone waxes, which may advantageously be substituted polysiloxanes, preferably with a low melting point. These silicone waxes are known and can be prepared in accordance with known methods. Among the commercial silicone waxes of this type, mention can be made in particular of those sold under the names Abilwax 9800, 9801 or 9810 (Goldschmidt), KF910 and KF7002 (Shin-Etsu), or 176-1118-3 and 176-11481 (General Electric), alkyl- or alcoxydimethicones such as the following commercial products: Abilwax 2428. 2434 and 2440 (Goldschmidt), or VP 1622 and VP 1621 (Wacker), as well as the (C20-C60) alkyldimethicones, in particular the (C30-C45) alkyldimethicones such as the silicone wax sold under the name SF-1642 by the company GE-Bayer Silicones.

Hydrocarbon-based waxes modified by silicone-based or fluorinated groups can also be used, such as for example: siliconyl candelilla, siliconyl beeswax and Fluorobeeswax from Koster Keunen.

The waxes may also be selected from fluorinated waxes.

According to a particular embodiment, the compositions according to the invention may comprise at least one wax known as tacky wax. As a tacky wax, use can be made of a C20-C40 alkyl (hydroxystearyloxy) stearate (the alkyl group comprising from 20 to 40 carbon atoms), alone or in a mixture, in particular a C20C40 alkyl 12-(12'-hydroxystearyloxy) stearate. Such a wax is in particular sold under the names "Kester Wax K 82 P®" and "Kester Wax K 80 P®" by the company Koster Keunen.

According to a preferred embodiment, the waxes are selected from hydrocarbon-based waxes, preferably selected from Carnauba wax, beeswax, jojoba wax, mimosa wax, sunflower wax and mixtures thereof.

Lipophilic Gelling Agents

Another type of lipophilic gelling agent is formed by copolymers of styrene and olefins such as ethylene, propylene and/or butylene, optionally associated with silicone or hydrocarbon solvents, as described in particular in the application WO 98/38981 and in U.S. Pat. No. 6,309,629. They comprise in particular the gelling agents based on sequenced terpolymers available from the company Penreco under the trade name VersageL®. Another type of lipophilic gelling agent consists of polyamides such as those identified by the INCI name polyamide-3 and in particular the polymers Sylvaclear® AF 1900V and PA 1200V available from the company Arizona Chemical, as well as those identified by the INCI name "Ethylenediamine/Hydrogenated Dimer Dilinoleate Copolymer Bis-Di-C14-18 Alkyl Amide" and available for example under the trade name Sylvaclear® A200V or Sylvaclear® A2614V from the company Arizona Chemical. The lipophilic gelling agent may in a variant be a bentone or a hydrophobic modified hectorite.

Colouring Agent

The emulsion according to the invention also comprises a colouring agent, preferably selected from pigments, nacres and soluble dyes, preferably soluble in water.

According to a preferred embodiment, the colouring agent is selected from pigments and/or nacres.

"Pigments" means white or coloured particles, mineral or organic, insoluble in an aqueous medium, intended to colour and/or opacify the emulsion and/or the resulting film.

The pigments may be white or coloured, mineral and/or organic.

The pigment may be an organic pigment. Organic pigment means any pigment that complies with the definition in Ullmann's Encyclopedia in the organic pigment chapter. The organic pigment may in particular be selected from the nitroso, nitro, azo, xanthene, quinoline, anthraquinone and phthalocyanine compounds, of the metallic complex type, isoindolinone, isoindoline, quinacridone, perinone, perylene, dicetopyrrolopyrrole, thioindigo, dioxazine, triphenylmethane, quinophthalone.

The organic pigment or pigments may be selected for example from carmine, carbon black, aniline black, melanin, azo yellow, quinacridone, phthalocyanine blue, sorgho red, the blue pigments codified in the Colour Index under the references CI 42090, 69800, 69825, 73000, 74100, 74160, the yellow pigments codified in the Colour Index under the references CI 11680, 11710, 15985, 19140, 20040, 21100, 21108, 47000, 47005, the green pigments codified in the Colour Index under the references CI 61565, 61570, 74260, the orange pigments codified in the Colour Index under the references CI11725, 15510, 45370, 71105, the red pigments codified in the Colour Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, 75470, the pigments obtained by oxidising polymerisation of indolic and phenolic derivatives as described in the patent FR 2 679 771.

These pigments may also be in the form of composite pigments as described in the patent EP 1 184 426. These composite pigments may be composed in particular of particles including an inorganic core covered at least partially with an organic pigment and at least one binder fixing the organic pigments to the core.

The pigment may also be a lacquer. Lacquer means the insolubilised dyes adsorbed on insoluble particles, the whole thus obtained remaining insoluble during use. By way of examples of lacquers, mention can be made of the product known by the following name: D & C Red 7 (CI 15 850:1).

The pigment may be a mineral pigment. Mineral pigment means any pigment that complies with the definition in Ullmann's Encyclopedia in the inorganic pigment chapter. Mention can be made, among the mineral pigments useful in the present invention, of zirconium or cerium oxides, as well as the oxides of zinc, iron (black, yellow or red) or chromium, manganese violet, ultramarine, chromium hydrate and ferric blue, titanium dioxide, metal powders such as aluminium powder and copper powder. The following mineral pigments can also be used: $Ta_2O_5$, $Ti_3O_5$, $Ti_2O_3$, TiO, $ZrO_2$ in a mixture with $TiCO_2$, $ZrO_2$, $Nb_2O_5$, $CeO_2$, ZnS.

The size of the pigment useful in the context of the present invention is generally between 10 nm and 10 µm, preferably between 20 nm and 5 µm, and more preferentially between 30 nm and 1 µm.

The colouring agent may also be a soluble dye, preferably soluble in water.

Among the water-soluble dyes, mention can be made of cochineal carmine or the products known by the following names: D & C Red 21 (CI 45 380), D & C Orange 5 (CI 45 370), D & C Red 27 (CI 45 410), D & C Orange 10 (CI 45 425), D & C Red 3 (CI 45 430), D & C Red 4 (CI 15 510), D & C Red 33 (CI 17 200), D & C Yellow 5 (CI 19 140), D & C Yellow 6 (CI 15 985). D & C Green (CI 61 570), D & C Yellow 1 0 (CI 77 002), D & C Green 3 (CI 42 053), D & C Blue 1 (CI 42 090).

The nacres may be selected from those conventionally present in make-up products, such as mica/titanium dioxide. In a variant, it may be a case of nacres based on mica/silica/titanium dioxide, based on synthetic fluorphlogopite/titanium dioxide (Sunshine® from Maprecos), calcium sodium borosilicate/titanium dioxide (Reflecks® from Engelhard) or calcium aluminium borosilicate/silica/titanium dioxide (Ronastar® from Merck).

The emulsion according to the invention may comprise from 0.0001 to 30% by weight colouring agent, preferably from 0.001 to 20% by weight, and more preferentially from 0.002 to 15% by weight, with respect to the total weight of emulsion according to the invention.

Fillers

The emulsion according to the invention may also comprise at least one filler. These fillers serve in particular to modify the rheology or the texture of the composition.

The fillers may be mineral or organic of any form, platelet, spherical or oblong, whatever the crystallographic form (for example flake, cubic, hexagonal, orthorhombic, etc.). Mention can be made of talc, mica, silica, silica surface treated by a hydrophobic agent, kaolin, polyamide powders (Nylon®) (Orgasol® from Atochem), poly-β-alanine and polyethylene, powders of tetrafluoroethylene polymers (Teflon®), lauroyl-lysine, starch, boron nitride, polymeric hollow microspheres such as those of polyvinylidene/acrylonitrile chloride such as Expancel® (Nobel Industries), acrylic acid copolymers (Polytrap® from Dow Corning) and silicon resin microbeads (Tospearls® from Toshiba, for example), polyorganosiloxane elastomer particles, precipitated calcium carbonate, magnesium carbonate and hydrogencarbonate, hydroxyapatite, hollow silica microspheres (Silica Beads® from Maprecos), glass or ceramic microcapsules, metallic soaps derived from carboxylic organic acids having from 8 to 22 carbon atoms, preferably from 12 to 18 carbon atoms, for example magnesium or lithium zinc stearate, zinc laurate or magnesium myristate.

Fibres

The emulsion according to the invention may also comprise at least one fibre, making it possible, in particular in the case of the use of a composition of the invention in the form of mascara, to obtain improvement to the extending effect.

"Fibre" means an object of length L and of diameter D such that L is greater than D, and preferably very much greater than D, D being the diameter of the circle in which the cross-section of the fibre is inscribed. In particular, the ratio L/D (or shape factor) is selected from the range from 3.5 to 2500, preferably from 5 to 500, and better from 5 to 150.

The fibres that can be used in the composition of the invention may be fibres of synthetic or natural origin, mineral or organic. They may be short or long, unitary or organised for example braided, hollow or solid. They may have any shape and in particular circular or polygonal (square, hexagonal or octagonal) in cross-section according to the specific application envisaged. In particular, the ends thereof are blunted and/or polished to avoid being injured.

In particular, the fibres have a length ranging from 1 µm to 10 mm, preferably from 0.1 mm to 5 mm and better from 0.3 mm to 3 mm. The cross-section thereof may be included in a circle with a diameter ranging from 2 nm to 500 µm, preferably ranging from 100 nm to 100 µm and better from 1 µm to 50 µm. The weight or count of the fibres is often given in denier or decitex and represents the weight in grams for 9 km of thread. Preferably, the fibres according to the invention have a count selected in the range from 0.01 to 10 denier, preferably from 0.1 to 2 denier and better from 0.3 to 0.7 denier.

The fibres that can be used in the compositions according to the invention can be selected from rigid or non-rigid fibres, they may be of synthetic or natural origin, mineral or organic.

Moreover, the fibres may be treated or not on the surface, enrobed or not, coloured or non-coloured.

By way of fibres that can be used in the compositions according to the invention, mention can be made of non-rigid fibres such as polyamide (Nylon®) fibres or rigid fibres such as the polyimide-amide fibres such as those sold by the names KERMEL® and KERMEL TECH® by the company RHODIA, or poly-(p-phenylene-terephthalamide) (or aramid) in particular sold by the name Kevlar® by the company DUPONT DE NEMOURS.

Cosmetic Active Agent

The emulsion according to the invention may also comprise at least one cosmetic active agent, which can be selected from the group consisting of vitamins, antioxidants, hydrating agents, anti-pollution agents, keratolytic agents, astringents, anti-inflammatories, whiteners, self-tanning agents and agents promoting microcirculation.

Examples of vitamins include vitamins A, B1, B2, B6, C and E and derivatives thereof, pantothenic and derivatives thereof and biotin.

Examples of antioxidants include ascorbic acid and derivatives thereof such as ascorbyl palmitate, ascorbyl tetraisopalmitate, ascorbyl glucoside, magnesium ascorbyl phosphate, sodium ascorbyl phosphate and ascorbyl sorbate; tocopherol and derivates thereof, such as tocopherol acetate, tocopherol sorbate and other tocopherol esters; BHT and BHA; esters of gallic acid, phosphoric acid, citric acid, maleic acid, malonic acid, succinic acid and fumaric acid, cephalin, hexametaphosphate, phytic acid, and plant extracts, for example roots of *Zingiber officinale* (ginger) such as the Blue Malagasy Ginger sold by the company Biolandes, *Chondrus crispus*, Rhodiola, *Thermus thermophilus*, maté leaf, oak wood, Kayu Rapet bark, Sakura leaves and ylang ylang leaves.

Examples of hydrating agents include polyethylene glycol, propylene glycol, dipropylene glycol, glycerine, butylene glycol, xylitol, sorbitol, maltitol and mucopolysaccharides, such as chondroitin sulfuric acid, hyaluronic acid of high or low molecular weight or hyaluronic acid potentialized by a silanol derivative such as the Epidermosil® active agent sold by the company Exymol, and mucoitinsulfuric acid; caronic acid; atelo collagen; chloresteryl-12-hydroxystearate; biliary salts, a principal component of NHF (natural hydration factor) such as a pyrrolidone carboxylic acid salt and a lactic acid salt, an amino acid analogue such as urea, cysteine and serine; a short-chain soluble collagen, PPG diglycerine, homo- and copolymers of 2-methacryloyloxyethylphosphorylcholine such as Lipidure HM and Lipidure PBM from NOF; allantoin; glycerine derivatives such as PEG/PPG/polybutylene Glycol-8/5/3 Glycerine from NOF sold by the trade name Wilbride® S753, or glycerylpolymethacrylate from Sederma sold under the trade name Lubragel® MS; the trimethylglycin sold under the trade name Aminocoat® by the company Asahi Kasei Chemicals, and various extracts of plants such as extracts of *Castanea sativa*, hydrolysed hazelnut proteins, polysaccharides of *Tuberosa polyanthes*, *Argania spinosa* kernel oil and extracts of nacres containing a conchiolin that are sold in particular by the company Maruzen (Japan) under the trade name Pearl Extract®.

Other examples of hydrating agents include the compounds stimulating the expression of matriptase MT/SP1, such as an extract of carob pulp, as well as the agents stimulating the expression of CERT, ARNT2 or FN3K or FN3K RP; the agents increasing the proliferation or differentiation of keratinocytes, either directly, or indirectly by stimulating for example the production of β-endorphins, such as the extracts of *Thermus thermophilus* or of *Theobroma cacao* bean hulls, water-soluble extracts of maize, peptide extracts of *Voandzeia subterranea* and niacinamide; epidermal lipids and agents increasing the synthesis of epidermal lipids, either directly, or by stimulating certain β-glucosidases that modulate the deglycosylation of lipid precursors such as glucosylceramide into ceramides, such as phospholipids, ceramides, lupin protein hydrolysates and dihydrojasmonic acid derivatives.

Examples of anti-pollution agents include extracts of *Moringa pterygosperma* seed extract (for example Purisoft® from LSN); shea butter extract (for example Detoxyl® from Silab), a mixture of extract of ivy, phytic acid and sunflower seed extract (for example Osmopur® from Sederma).

Examples of keratolytic agents include the α-hydroxyacids (for example the glycolic, lactic, citric, malic, mandelic or tartric acids), and the β-hydroxyacids (for example salicylic acid), and esters thereof, such as the C12-13 alkyl lactates, and the extracts of plants containing these hydroxyacids, such as extracts of *Hibiscus sabdariffa*.

Examples of astringents include extracts of hamamelis.

Examples of anti-inflammatories include bisabolol, allantoin, tranexamic acid, zinc oxide, sulfur oxide and derivates thereof, chondroitin sulfate, glycyrrhizinic acid and derivatives thereof such as glycyrrhizinates.

Examples of whiteners include arbutin and derivatives thereof, ferulic acid (such as Cytovector®: water, glycol, lethicin, ferulic acid, hydroxyethylcellulose, sold by BASF) and derivatives thereof, kojic acid, resorcinol, lipoic acid and derivatives thereof such as resveratrol diacetate monolipoate as described in the patent application WO 2006/134282, ellagic acid, leucodopachrome and derivates thereof, vitamin B3, linoleic acid and derivatives thereof, ceramides and homologues thereof, a peptide as described in the patent application WO 2009/010356, a bioprecursor as described in the patent application WO 2006/134282 or a tranexamate salt such as the cetyl tranexamate hydrochloride salt, an extract of liquorice (extract of *Glycyrrhiza glabra*), which is sold in particular by the company Maruzen under the trade name Liquorice extract®, a whitener also having an antioxidant effect, such as the vitamin C compounds, including the ascorbate salts, the ascorbyl esters of fatty acids or of ascorbic acid, and other derivates of ascorbic acid, for example ascorbyl phosphates, such as magnesium ascorbyl phosphate and sodium ascorbyl phosphate, or the esters of ascorbic acid saccharide, which include, for example, ascorbyl-2-glucoside, L-ascorbate of 2-O-alpha-D-glucopyranosyl, or L-ascorbate of 6-O-beta-D-galactopyranosyl. An active agent of this type is sold in particular by the company DKSH under the trade name Ascorbyl glucoside®.

An example of a self-tanning agent is DHA.

Examples of agents favouring microcirculation include an extract of lupin (such as Eclaline® from Silab), of butcher's broom, of horse chestnut, of ivy, of ginseng or of melilot, caffeine, nicotinate and derivatives thereof, an extract of *Corallina officinalis* alga such as the one sold by CODIF; and mixtures thereof. These agents active on skin microcirculation may be used to avoid dulling of the colour and/or to improve homogenisation and radiance of the colour.

The emulsion according to the invention may comprise from 0.0001 to 10% by weight cosmetic active agent, preferably from 0.001 to 5% by weight, and more preferentially from 0.002 to 1% by weight, with respect to the total weight of the emulsion according to the invention.

Additives

The emulsion according to the invention may comprise other ingredients provided that they do not interfere with the required properties of the emulsion. These other ingredients may for example be preservatives, pH adjusters such a citric acid or arginine, antimicrobial agents, perfumes, sun blockers, and mixtures thereof.

Preparation Method

Another object of the present invention is a method for preparing an emulsion according to the invention, comprising:
- mixing water, plasticiser and optionally film-forming agent and optionally a preservative under stirring at a temperature higher than or equal to 90° C.,
- adding starch under stirring until a gel forms,
- optionally adding a gelling agent,
- optionally adding colouring agent,
- heating wax to a temperature higher than or equal to 90° C. to enable said wax to melt,
- adding said molten wax and emulsifier to the mixture comprising water and plasticiser under stirring to form the emulsion,
- cooling the emulsion obtained to ambient temperature under stirring,
- optionally adjusting the pH, and
- optionally adding alcohol.

Method for Making Up Keratin Materials

The present invention also relates to a method for making up keratin materials, in particular keratin fibres such as the eyelashes or eyebrows, consisting in applying to said keratin materials, in particular keratin fibres such the eyelashes or eyebrows, an emulsion according to the invention.

EXAMPLES

Example 1: Mascara

A mascara having the composition presented in the following Table 1 was prepared:

TABLE 1

| INCI name | Content (% by weight) |
| --- | --- |
| PEA STARCH (LYCOAT NG 720 FROM THE COMPANY ROQUETTE FRÈRES) | 17.34 |
| GLYCERINE | 10 |
| SORBITOL & WATER (70% MA) | 5 |
| PENTYLENE GLYCOL | 2.5 |
| CERA CARNAUBA (COPERNICIA CERIFERA (CARNAUBA) WAX) | 12.5 |
| PEG 8-BEESWAX (APIFIL CG from GATTEFOSSÉ) | 8.75 |
| PIGMENTS | 10 |
| DEMINERALISED WATER | 33.0 |
| PRESERVATIVE | 0.9 |

The mascara was prepared in accordance with the following protocol:
- weighing the aqueous phase comprising water, glycerine, sorbitol, pentylene glycol and preservative and heating it at 90° C. under stirring in a rotor stator at 245 rpm,
- adding LYCOAT NG 720 under stirring for 5 min at 245 rpm until the gel forms,
- adding the pigments under stirring in a rotor stator at 350 rpm,
- melting the waxes (carnauba and emulsifier wax) at 90° C. under Rayneri stirring,
- introducing the molten waxes into the aqueous phase in a rotor stator at 350 rpm to form the emulsion,
- leaving the formula to cool to ambient temperature under stirring with a deflocculator.

The mascara obtained is fluid and homogeneous, it is applied easily. The make-up result is extending and curving. It can be removed easily by peeling off or with water.

Example 2: Mascara

A mascara having the composition presented in the following Table 2 was prepared:

TABLE 2

| INCI name | Content (% by weight) |
| --- | --- |
| PREGELATINISED PEA STARCH (LYCOAT RS 720 FROM THE COMPANY ROQUETTE FRÈRES) | 6.0 |
| GLYCERINE | 10 |
| SORBITOL & WATER (70% MA) | 3.5 |
| PENTYLENE GLYCOL | 2.5 |
| ETHYL ALCOHOL | 3.0 |
| POLOXAMER 407 (AND) PPG-12/SMDI COPOLYMER (ExpertGel 412) | 3.0 |
| SODIUM POLYITACONATE & AQUA (WATER)& SODIUM ITACONATE & SODIUM PERSULFATE & SODIUM SALTS OF CITRACONIC/MESACONIC ACIDS (REVCARE NE 100S) | 5.0 |
| CERA CARNAUBA (COPERNICIA CERIFERA(CARNAUBA) WAX) | 6.0 |
| PEG 8-BEESWAX (APIFIL CG from GATTEFOSSÉ) | 9.0 |
| PIGMENTS | 10 |
| FILLERS | 1.1 |
| DEMINERALISED WATER | 39.70 |
| PRESERVATIVE | 0.7 |
| 25% SODA SOLUTION | 0.5 |

The mascara was prepared in accordance with the following protocol:
- weighing the aqueous phase comprising water, glycerine, sorbitol, pentylene glycol, alcohol, ExpertGel 412, REVCARE NE 100S and preservative and heating it at 90° C. under stirring in a rotor stator at 245 rpm,
- adding LYCOAT RS 720 under stirring for 5 min at 245 rpm until gel forms,
- adding the pigments and the fillers under stirring in a rotor stator at 350 rpm,
- melting the waxes at 90° C. under Rayneri stirring,
- introducing the molten waxes into the aqueous phase in a rotor stator at 350 rpm to form the emulsion,
- leaving the formula to cool to ambient temperature under stirring with a deflocculator,
- adjusting the pH with a soda solution, and
- adding alcohol.

The mascara obtained is fluid and homogeneous, it is easily applied. The make-up result is extending and curving. It can be removed easily by peeling off or with water.

The invention claimed is:

1. A wax-in-water cosmetic emulsion comprising:
   - at least one leguminous starch having an amylose content greater than or equal to 30%,
   - at least one plasticiser selected from polyols,
   - at least one wax,
   - at least one emulsifier,
   - at least one colouring agent, and
   - water.

2. The emulsion according to claim 1, wherein the at least one leguminous starch has a Brookfield viscosity in aqueous dispersion at 25° C. with 20% dry matter of between 10 and 10000 mPa·s.

3. The emulsion according to claim 1, wherein the at least one leguminous starch has an amylose content in a range from 30% to 45%.

4. The emulsion according to claim 1, wherein the at least one leguminous starch is selected from pea starches, chickpea starches, broad-bean starches, horse-bean starches, haricot-bean starches or lentil starches.

5. The emulsion according to claim 1, wherein the at least one leguminous starch is a hydrolysed and hydroxypropylated leguminous starch.

6. The emulsion according to claim 1, wherein the at least one leguminous starch is present in a dry-matter content of between 0.1% and 25% by weight, with respect to the total weight of the emulsion.

7. The emulsion according to claim 1, wherein the polyols are selected from propylene glycol, butylene glycol, pentylene glycol, pentanediol, isoprene glycol, neopentyl glycol, glycerol, polyethylene glycols (PEGs) having from 4 to 8 ethylene glycol units and/or sorbitol.

8. The emulsion according to claim 1, wherein the polyols are present in a proportion ranging from 8 to 25% by weight, with respect to the total weight of the emulsion.

9. The emulsion according to claim 1, wherein the wax is selected from hydrocarbon waxes such as beeswax, lanolin wax and Chinese insect waxes; rice wax, carnauba wax, candellila wax, ouricurry wax, Alfa wax, cork-fibre wax, sugar cane wax, Japan wax and sumac wax; montan wax, microcrystalline waxes, paraffins and ozokerite; polyethylene waxes, waxes obtained by Fisher-Tropsch synthesis and waxy copolymers as well as esters thereof.

10. The emulsion according to claim 1, wherein the emulsifying agent has an HLB of between 8 and 20, and is selected from fatty acid esters and oxyethylenated and/or oxypropylenated sorbitol ethers, lysophospholipids, emulsifying waxes selected from self-emulsifying waxes or hydrolysed waxes, and mixtures thereof.

11. The emulsion according to claim 1, wherein the emulsion comprises from 25 to 60% by weight water, with respect to the total weight of the emulsion.

12. The emulsion according to claim 1, further comprising a hydrophilic gelling agent, selected from polysaccharides, protein derivatives, synthesis or semi-synthesis gels of polyesters, polyacrylates or polymethacrylates and derivatives thereof.

13. The emulsion according to claim 1, further comprising an additional film-forming agent other than starch.

14. The emulsion according to claim 1, further comprising at least one mono-alcohol having 1 to 5 carbon atoms.

15. The emulsion according to claim 1, wherein the colouring agent is selected from pigments and/or nacres and/or soluble dyes.

16. A method for preparing the emulsion according to claim 1, comprising:
    mixing the water, the plasticiser and optionally the film-forming agent and optionally a preservative under stirring at a temperature higher than or equal to 90° C.,
    adding the starch under stirring until a gel forms,
    optionally adding a gelling agent,
    optionally adding the colouring agent,
    heating the wax to a temperature higher than or equal to 90° C. to enable said wax to melt,
    adding said molten wax and the emulsifying agent to the mixture comprising the water and the plasticiser under stirring to form the emulsion,
    cooling the emulsion obtained to ambient temperature under stirring,
    optionally adjusting the pH, and
    optionally adding alcohol.

17. A method for making up keratin fibres selected from eyelashes or eyebrows, consisting of applying to said keratin fibres, the emulsion according to claim 1.

18. A method for conferring on keratin fibres, an extending and curving effect, comprising applying to the keratin fibres the emulsion according to claim 1.

19. The emulsion according to claim 7, wherein the polyols are glycerol and sorbitol.

20. The emulsion according to claim 7, wherein the polyols are a mixture with pentylene glycol.

* * * * *